United States Patent [19]

Withycombe et al.

[11] 4,156,029

[45] * May 22, 1979

[54] ALPHA-SUBSTITUTED ALKYLIDENE METHIONALS AND USES THEREOF IN FOODSTUFFS AND FLAVORS FOR FOODSTUFFS

[75] Inventors: Donald A. Withycombe, Lincroft; Anne Hruza, Bricktown; Manfred H. Vock, Locust; Christopher Giacino, Califon; Braja D. Mookherjee, Holmdel; Alan O. Pittet, Atlantic Highlands; William L. Schreiber, Jackson, all of N.J.

[73] Assignee: International Flavors & Fragrances Inc., New York, N.Y.

[*] Notice: The portion of the term of this patent subsequent to Jan. 30, 1996, has been disclaimed.

[21] Appl. No.: 902,389

[22] Filed: May 3, 1978

Related U.S. Application Data

[60] Continuation-in-part of Ser. No. 827,265, Aug. 24, 1977, which is a division of Ser. No. 753,462, Dec. 22, 1976, Pat. No. 4,064,279.

[51] Int. Cl.$^2$ ............................................. A23L 1/236
[52] U.S. Cl. ..................................... 426/535; 260/599
[58] Field of Search ......................... 426/535; 260/599

[56] References Cited

U.S. PATENT DOCUMENTS

4,064,279 12/1977 Wethycombe et al. ............. 426/535

*Primary Examiner*—Joseph M. Golian

*Attorney, Agent, or Firm*—Liberman, Arthur L.; Franklin D. Wolffe

[57] ABSTRACT

Described are mixtures of cis and trans isomers of 2-[(methylthio)methyl]-3-phenyl-2-propenal having the structures:

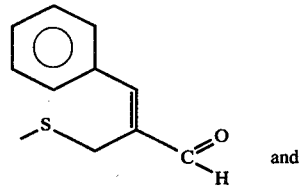

and

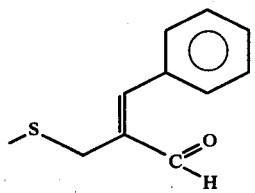

The ratio of cis to trans isomer being from 7:3 up to 9.5:0.5 wherein augmenting and enhancing the flavors and aroma of meat extract, meat, hydrolyzed vegetable protein, nut and chocolate flavored foodstuff by augmenting or enhancing the sweet, meat extract like, hydrolyzed vegetable protein like and beef broth like aroma and sweet, meat extract like, hydrolyzed vegetable protein like, beef broth like, and monosodium glutamate like flavor characteristics with mouthfeel effects.

6 Claims, 10 Drawing Figures

FIG.1A
EXAMPLE I

FIG.1B
EXAMPLE I

FIG. 2A
EXAMPLE I

FIG. 2B
EXAMPLE I

FIG. 4

IR SPECTRUM FOR EXAMPLE IIA

FIG. 8
MASS SPECTRUM FOR EXAMPLE IIB

ALPHA-SUBSTITUTED ALKYLIDENE METHIONALS AND USES THEREOF IN FOODSTUFFS AND FLAVORS FOR FOODSTUFFS

This application is a continuation-in-part of application for United States Letters Patent, Ser. No. 827,265, filed on Aug. 24, 1977 which, in turn, is a division of application for United States Letters Patent, Ser. No. 753,462, filed on Dec. 22, 1976, now U.S. Pat. No. 4,064,279, issued on Dec. 20, 1977.

BACKGROUND OF THE INVENTION

The present invention relates to alpha-substituted alkylidene methionals and novel compositions using such compounds to augment or enhance the flavor and/or aroma of foodstuffs.

There has been considerable work performed relating to substances useful in augmenting or enhancing the flavor and/or aroma of various consumable materials including foodstuffs. These substances are used to supplement the use of natural materials, some of which may be in short supply and/or provide more uniform properties in the finished product. The following flavor and aroma notes are desirable, particularly in meat, chocolate and nutty flavored foodstuffs:

Aroma sweet;
Meat extract-like;
Hydrolyzed vegetable protein-like; and
Beef broth-like.

Flavor

Sweet;
Meat extract-like;
Hydrolyzed vegetable protein-like;
Beef broth-like;
Monosodium glutamate-like enhancement with a good mouthfeel effect.

2,8-dithianon-4-ene-4-carboxaldehyde having the structure:

has been isolated from hydrolyzed vegetable protein distillate and has been found to have a sweet, meaty, hydrolyzed vegetable protein taste at 0.02 ppm, the threshold level. At 0.5 ppm 2,8-dithianon-4-ene-4-carboxaldehyde has a liver sausage, cabbage, potato, metallic, hydrolyzed vegetable protein-like, beef broth and methional aroma with liver sausage, cabbage, potato, hydrolyzed vegetable protein-like, beef broth-like, limburger cheese-like and methional-like flavor. The compound naturally-occurring in hydrolyzed vegetable protein distillate, has flavor and aroma nuances many of which are different in kind from the flavor and aroma nuances of the compounds of this invention.

Buttery, in an article entitled "Some Unusual Volatile Carbonyl Components of Potato Chips", J. Agr. Food Chem., Vol. 21, No. 1, 1973, pages 31–33, discloses compounds having the structures:

The compounds disclosed by Buttery are considered to have structures different in kind from the structures of the compounds of the instant invention. Furthermore, the flavor and aroma nuances of these compounds of Buttery are different in kind from the flavor and aroma nuances of the compounds of the instant invention.

Japanese Pat. No. J7 8,001,827, issued Jan. 23, 1978 to the General Foods Corporation, discloses a flavor enhancing composition for foodstuffs comprising 45–55% by weight hydrolyzed corn protein, 35–45% sodium chloride, 1–7% hydrolyzed soy protein, 1–5% beef flavor and 1–5% onion flavor and further states that such a composition has flavor enhancing properties similar to those of monosodium glutamate. The composition of Japanese Pat. No. J7 8,001,827, however, is different in kind from the isomer composition of our invention; not only from a chemical point of view but also insofar as the comparative organoleptic properties of these compositions are concerned.

THE INVENTION

The present invention comprises novel compositions and foodstuffs containing mixtures of cis and trans isomers of alpha-substituted alkylidene methionals having the structure:

wherein one of $R_1$ or $R_2$ is phenyl having the structure:

and the other of $R_1$ or $R_2$ is hydrogen, the specific embodiments of which are described hereinafter by way of example and in accordance with which it is now preferred to practice the invention.

Such alpha-substituted alkylidene methionals are obtained by reacting benzaldehyde with methional in the presence of a base according to the following reaction:

wherein $R_1$ and $R_2$ are as defined as above. This reaction takes place in the presence of a base such as alkali metal hydroxide or an alkali earth metal hydroxide. The reaction is well known as an "aldol condensation" type reaction. Examples of base which can be used in this reaction are lithium hydroxide, sodium hydroxide, potassium hydroxide and barium hydroxide. The concentration of base may vary between 0.1 molar up to 5 molar with a preferred concentration range of from 0.3 molar up to 0.8 molar. The reaction temperature range is between −10° C. and 50° C. with a temperature of reaction being a function of the particular base catalyst used.

The mole ratio of methional to benzaldehyde is not critical, but most convenient is a mole ratio of 1:1.

At the end of this reaction the reaction mass is "worked up" by extracting the reaction product with a solvent such as methylene chloride and then treating the organic layer with weak acid and weak base and finally fractionally distilling the resulting reaction product, e.g., by means of vacuum distillation.

Figure 1A:
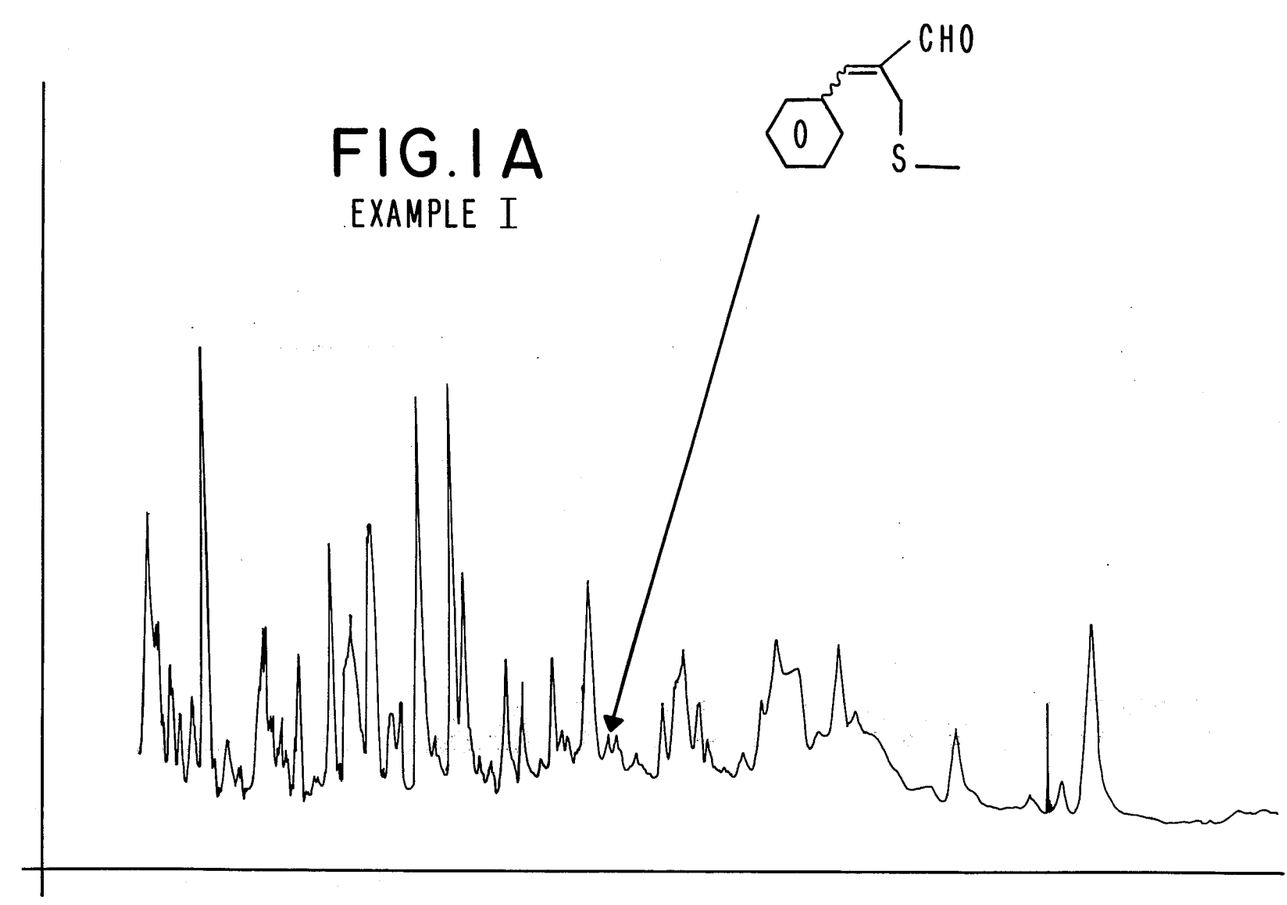
FIG. 1A illustrates the GLC spectrum for 2-[(methylthio)methyl]-3-phenyl-2-propenal produced according to Example I.
Figure 1B:
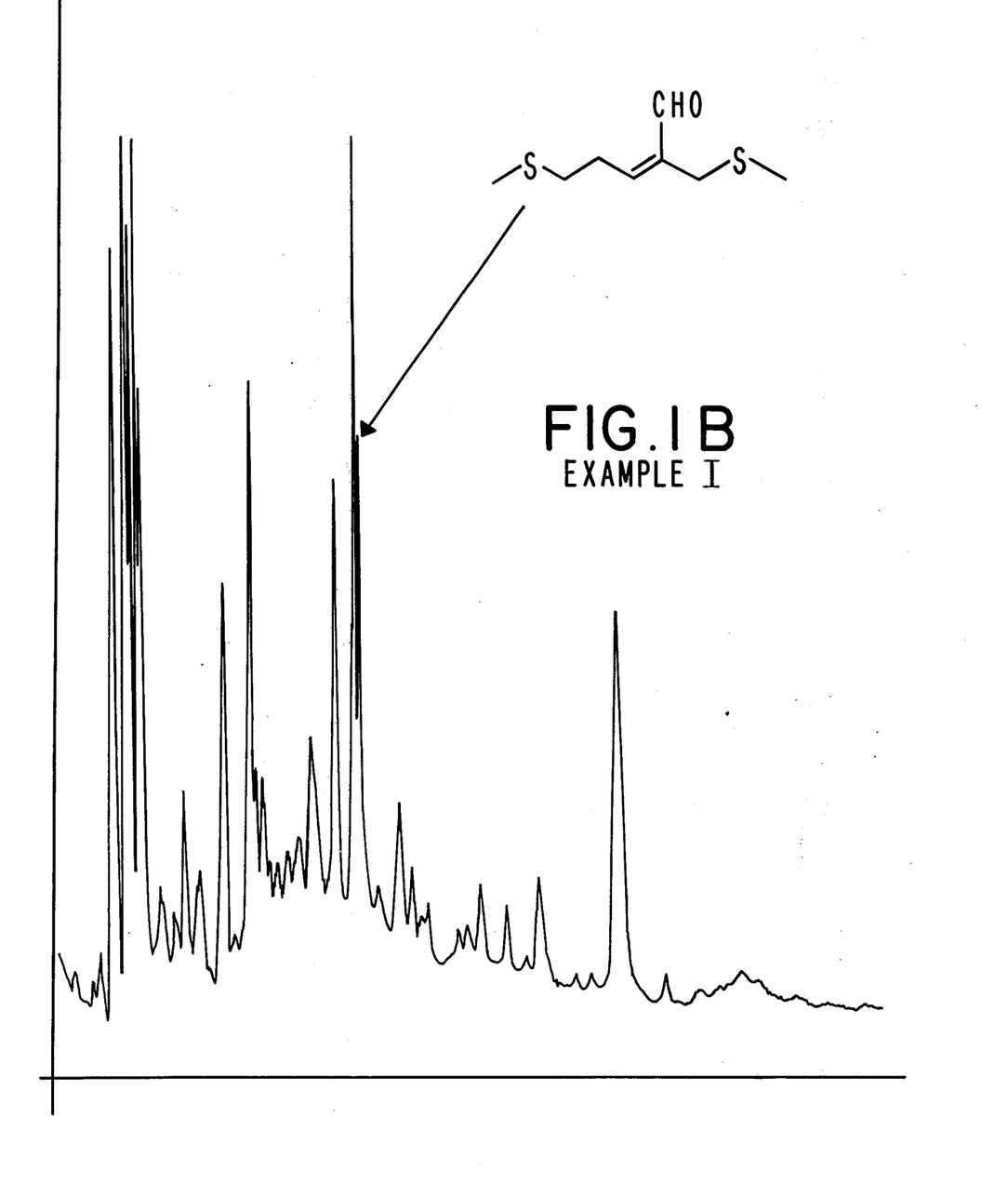
FIG. 1B illustrates the GLC spectrum for the neutral fraction containing 2,8-dithianon-4-ene-4-carboxaldehyde.

The alpha-substituted alkylidene methionals produced using the aforementioned process of our invention are mixtures of cis and trans isomers in a ratio from 70–95% cis isomer having the structure and from 30–5% of the isomer having the structure On the other hand, the distillate of hydrolyzed vegetable protein (as produced according to Example I, infra), appears to contain 2,8-dithianon-4-ene-4-carboxaldehyde and in addition may also contain cis and/or trans isomers of 2-[(methylthio) methyl]-3-phenyl-2-propenal. The possibility of the presence of the foregoing materials in the distillate of hydrolyzed vegetable protein is indicated in various peaks in FIG. 1A and 1B, respectively. The possible presence of such compounds in hydrolyzed vegetable protein distillate is not considered to infer that these compounds in a given cis:trans isomer ratio can be used as foodstuff flavorants or that they can be used in order to augment or enhance the flavor or aroma of a foodstuff. Hydrolyzed vegetable protein contains a large number of compounds which are not useful for their organoleptic properties; for augmenting or enhancing the aroma or taste of foodstuffs.

The compounds of our invention, the mixtures of cis and trans isomers of 2-[methylthio)methyl]-3-phenyl-2-propenal as well as the 5-methyl-alpha[(methylthio)methyl]-2-furanacrolein of the parent cases of the instant continuation-in-part application represent an advance in the art and have unexpected and unobvious and advantageous properties with respect to hydrolyzed vegetable protein insofar as the organoleptic properties of these materials are concerned. Thus, when hydrolyzed vegetable protein is compared with a mixture of cis and trans 2[(methylthio)methyl]-3-phenyl-2-propenal of our invention (87:13 cis:trans ratio) and with 5-methyl-alpha[(methylthio) methyl]-2-furanacrolein the following results are achieved:

At 0.02 ppm of 5-methyl-alpha[(methylthio) methyl]-2-furanacrolein, a sweet, light, sulfury, cooked potato, cabbage, minty, metalic aroma and taste is achieved and 0.5 ppm a sweet, light sulfury, cooked potato, cabbage, minty and metalic aroma and taste is achieved. At 1 ppm of a mixture of cis and trans 2-[(methylthio)methyl]-3-phenyl-2-propenal of our invention (87:13 cis:trans ratio), a green, weedy aroma exists with monosodium glutamate-like characteristics and in addition a sweet mouthfeel effect exists which give this material a lasting aroma and taste and causes it to be very interesting and suitable for use in conjunction with meat extract. When the mixture of cis and trans 2-[(methylthio)-methyl]-3-phenyl-2-propenal of our invention is added to a 0.1% solution of hydrolyzed vegetable protein the mouthfeel/monosodium glutamate-like effect and the strength of the solution is increased (at 2 parts per million of the mixture of cis and trans 2-[(methylthio)methyl]-3-phenyl-2-propenal of our invention). On the other hand at a level of 0.1% hydrolyzed vegetable protein alone, the notes of both materials, the mixture of cis and trans 2-[(methylthio)methyl]-3-phenyl-2-propenal of our invention and 5-methyl-alpha[(methylthio)-methyl-2-furan acrolein such as the green vegetable notes of the mixtures of the cis and trans 2-[(methylthio)-methyl]-3-phenyl-2-propenal of our invention and the sulfury metallic notes of 5-methyl-alpha-[(methylthio)methyl]-2-furan acrolein are not present in hydrolyzed vegetable protein. Both materials, the mixtures of cis and trans 2-[(methylthio)methyl]-3-phenyl-2-propenal of our invention and 5-methyl-alpha[(methylthio) methyl]-2-furan acrolein are suitable for augmenting the aroma and taste of hydrolyzed vegetable protein, although their organoleptic properties are different. Both materials, the mixture of cis and trans 2-[(methylthio)-methyl]-3-phenyl-2-propenal of our invention and 5-methyl-alpha-[(methyl-thio)methyl]-2-furan acrolein represent an advance in the art over hydrolyzed vegetable protein itself and have unexpected, unobvious and advantageous organoleptic properties with respect to hydrolyzed vegetable protein.

When the alpha-substituted alkylidene methionals of our invention are used as food flavor adjuvants, or are used to augment or enhance the flavor or aroma characteristics of foodstuffs, the nature of the co-ingredients included with the said alpha-substituted alkylidene methionals in formulating the product composition will also serve to augment the organoleptic characteristics of the ultimate foodstuff treated therewith.

As used herein in regard to flavors, the term "augment" in its various forms means "supplying or imparting flavor character or note to otherwise bland, relatively tasteless substances or augmenting the existing flavor characteristic where a natural flavor is deficient in some regard or supplementing the existing flavor impression to modify its quality, character or taste."

As used herein in regard to food flavors, the term "enhance" is used herein to mean the intensification of a flavor or aroma characteristic or note without the modification of the quality thereof. Thus, "enhancement" of a flavor or aroma means that the enhancement agent does not add any additional flavor note.

As used herein the term "foodstuff" includes both solids and liquids, and ingestible materials or chewable but non-ingestible materials such as chewing gum. Such materials usually do, but need not, have nutritional value. Thus, foodstuffs include soups, convenience foods, beverages, gelatin desserts, dairy products, candies, vegetables, cereals, soft drinks, snacks and the like.

Substances suitable for use herein as co-ingredients or flavoring adjuvants are well known in the art for such use, being extensively described in the relevant literature. Apart from the requirements that any such materials be organoleptically compatible with the alpha-substituted alkylidene methionals, non-reactive with the alpha-substituted alkylidene methionals of our invention and "ingestibly" acceptable and thus non-toxic or otherwise non-deleterious, nothing particularly critical resides in the selection thereof. Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditions include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include vanillin, ethyl vanillin, diacetyl, phenethyl 2-furoate, maltol, neryl butyrate, amyl butyrate, allyl caproate, citral, 4-methylthiobutanal, 2-trans hexenal, dimethyl sulfide, linalool, acetic acid, methyl sulfide, acetaldehyde, isovaleraldehyde, isoamyl alcohol, acetic acid, lactones, including δ-decalactone, δ-undecalactone and γ-nonalactone, isoamyl esters including the acetate, butyrate and octanoate, pyrazines such as 2,6-dimethyl pyrazine, 2-ethyl-3-methyl pyrazine, 2,3-diethyl-5-methyl pyrazine, 2-ethyl-3-acetyl pyrazine, tetramethyl pyrazine, 2-methyl pyrazine, amyl octanoate, benzoic acid, pyridine, phenylacetic acid, cinnamyl esters such as the propionate, 4-phenyl-3-butene-2-one, 3-phenyl-2-pentenal, 3-phenyl-4-pentenal, 2-phenyl-2-methyl-4-pentenal, 2-phenyl-4-pentenal, 2-phenyl-4-pentenal dimethyl acetal, 2-isobutylthiazole, 2-(secondary butyl) thiazole, 2-(i-propyl) thiazole and 2-(n-propyl) thiazole. These are combined in proportions requisite to obtain the desired effect as illustrated further hereinbelow.

As will be appreciated by those skilled in the art, the amount of alpha-substituted alkylidene methionals employed in a particular instance can vary over a relatively wide range whereby to its desired organoleptic effects having reference to the nature of the product are achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e., sufficient to alter the organoleptic characteristics of the parent composition.

The use of insufficient quantities of alpha-substituted alkylidene methionals will, of course, substantially vitate any possibility of obtaining the desired results while excess quantities prove needlessly costly and in extreme cases may disrupt the flavor-aroma balance, thus proving self-defeating. Accordingly, the terminology "effective amount " and "sufficient amount" is to be accorded a significance in the context of the present invention consistent with the obtention of desired flavoring effects.

Thus, and with respect to ultimate food compositions, it is found that quantities of alpha-substituted alkylidene methionals ranging from a small but effective amount, e.g., about 0.02 parts per million up to about 50 parts per million by weight based on total composition (more preferably from about 0.2 ppm up to about 25 ppm) are suitable. Concentrations in excess of the maximum quantity stated are not normally recommended, since they fail to prove commensurate enhancement of organoleptic properties. In those instances, wherein the alpha-substituted alkylidene methionals is added to the foodstuff as an integral component of a flavoring composition, it is, of course, essential that the total quantity of flavoring composition employed be sufficient to yield an effective alpha-substituted alkylidene methional concentration in the foodstuff product.

Food flavoring compositions prepared in accordance with the present invention preferably contain the alpha-substituted alkylidene methional in concentrations ranging from about 0.1% up to about 15% by weight based on the total weight of said flavoring composition.

The compositions described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the alpha-substituted alkylidene methionals with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix, are obtained by mixing the dried solid components, e.g., starch, sugar and the like and alpha-substituted alkylidene methionals in a dry blender until the requisite degree of uniformity is achieved.

It is presently preferred to combine with the alpha-substituted alkylidene methionals, the following adjuvants:
Acetaldehyde;
Isobutyraldehyde;
Isovaleraldehyde;
Methyl sulfide;
Methyl disulfide;
Isobutyl acetate;
Phenylethyl acetate;
Diacetyl;
Acetophenone;
Furfural (50%);
Benzaldehyde;
Phenylacetaldehyde;
Isoamyl alcohol;
Phenylethyl alcohol;
Gamma-butyrolactone;
3-Phenyl-4-pentenal;
3-Phenyl-3-pentenal;
3-Phenyl-2-pentenal;
Methyl pyrazine;
Tetramethyl pyrazine;
Trimethylpyrazine;
2,6-Dimethylpyrazine;
2-Ethyl-3-methylpyrazine;
2-Ethyl-3,5-dimethylpyrazine;
2-Ethyl-3,6-dimethylpyrazine;
2-Ethyl-5-methylpyrazine;
2-Ethyl-3-acetyl pyrazine;
2-(i-butyl) thiazole;
2-(i-propyl) thiazole;
2-(n-propyl) thiazole;
2-Phenyl-4-pentenal;
2-Phenyl-4-pentenaldimethylacetal;
4-Methylthiobutanal;
trans-2-hexenal;
Hydrolyzed vegetable protein;
Monosodium glutamate;
Black pepper oil;
Nutmeg oil;
Celery oil;
Lemon oil;
Mustard oil.

The following examples are given to illustrate embodiments of the invention as it is presently preferred to practice it. It will be understood that these examples are illustrative and that the invention is not to be considered as restricted thereto except as indicated in the appended claims.

EXAMPLE I

PREPARATION AND ANALYSIS OF DISTILLATE OF HYDROLYZED VEGETABLE PROTEIN

240 Pounds of Nestle 4-BE hydrolyzed vegetable protein is intimately admixed with 240 pounds deionized water. The resulting mixture is metered into a Turbofilm evaporator and distilled under atmospheric pressure whereby 20% is recovered as an aqueous distillate and 80% is discarded. The aqueous distillate is then subjected to extraction in a 22 liter round bottom liquid-liquid extractor. The extractor is charged with the aqueous distillate and saturated with sodium chloride. The resulting mixture is extracted with diethyl ether. The ether extract is then evaporated using a 5 liter Keuderna-Danish evaporator. The resulting material is then fractionated into acidic, phenolic, basic and neutral components. Each of the fractions is analyzed using GLC, NMR, IR and mass spectral analyses. Evidence is obtained by the foregoing analyses which indicate that 2,8-dithianon-4-ene-4-carboxaldehyde is present in the neutral fraction and that cis and/or trans isomers of 2-[(methylthio)methyl]-3-phenyl-2-propenal may be present. The GLC spectrum for the neutral fraction containing 2,8-dithianon-4-ene-4-carboxaldehyde is set forth in FIG. 1B and the MS analysis is set forth in FIG. 2B. Evidence for the existence of cis and/or trans isomers of 2-[(methylthio)methyl]-3-phenyl-2-propenal is set forth in the GLC spectrum of the neutral fraction in FIG. 1A and the MS analysis of the compounds is set forth in FIG. 2A.

Figure 2A:
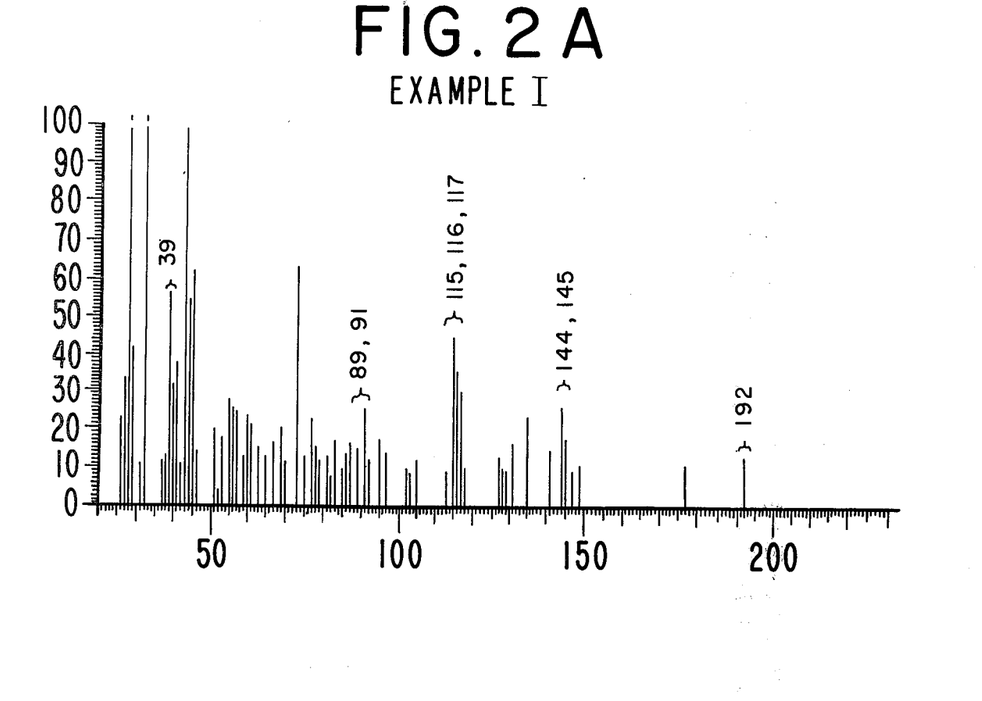
FIG. 2A illustrates the Mass Spectrum setting forth peaks including those of 2-[(methylthio)methyl]-3-phenyl-2-propenal produced according to Example I.
Figure 2B:
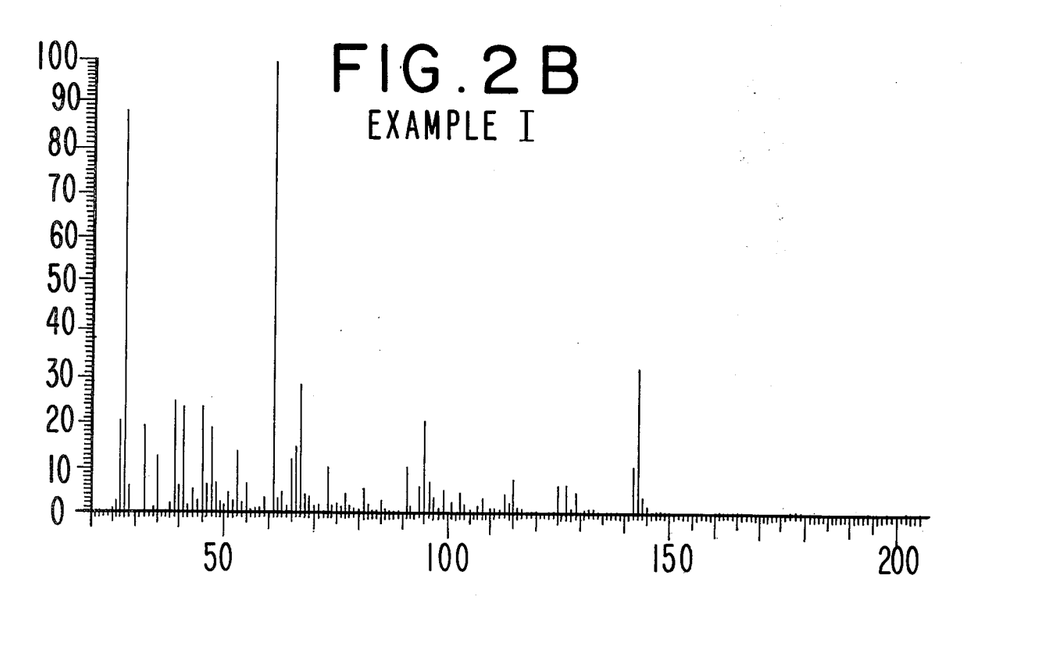
FIG. 2B illustrates the Mass Spectrum of 2,8-dithianon-4-ene-4-carboxaldehyde isolated from the neutral fraction.

In FIG. 2A, the peaks indicated by the numbers 39, (89, 91), (115, 116, 117), (144, 145) and 192 have been interpreted as a "tentative" identification of 2-[(methylthio)methyl]-3-2-propenal. FIG. 2A sets forth a "mixed" mass spectrum setting forth peaks including those for the said 2-[(methylthio)methyl]-3-2-propenal.

EXAMPLE IIA

PREPARATION OF 100% CIS-2-[(METHYLTHIO)METHYL]-3-PHENYL-2-PROPENAL

Reaction:

(all cis isomer)

Into a 100 ml three necked reaction flask equipped with stirrer, thermometer and addition funnel is charged a solution of 0.5 grams of potassium hydroxide in 10 ml methanol. Benzaldehyde (10.0 grams) is added as the mixture is cooled to 5°-10° C. Methional (10.0 grams) is then added dropwise while maintaining the reaction temperature at 5°-10° C. The mixture is then allowed to warm to room temperature and stirred for a period of 1 hour. Most of the solvent is evaporated at reduced pressure and the mixture is partitioned between water and ether. The organic layer is washed several times with water and once with saturated brine. The solvent is evaporated leaving a yelow oil which is distilled to give 6.1 grams product, boiling point 104°-111° C. (0.4 mm Hg).

The distillate is crystallized from ether-hexane and then recrystallized twice from ether to give 1.5 grams of colorless needles, melting point 30.4°-31.0° C. The NMR data is as follows:

| Chemical Shift (ppm) | Assignment | Integration |
|---|---|---|
| 2.12 (s) | CH$_3$S | 3H |
| 3.56 (s) | =C—CH$_2$—S— | 2H |
| 7.62–7.19 (m) | aromatic protons + olefinic protons | 6H |
| 9.53 (s) | HC=O | 1H |

The Infrared absorption bands are as follows: cm$^{-1}$ 695, 740, 755, 865, 1125, 1200, 1320, 1430, 1450, 1620, 1680, 2920.

The Mass Spectral data is as follows:

| m/e | Relative Intensity (%) |
|---|---|
| 29 | 22 |
| 39 | 24 |
| 45 | 22 |
| 63 | 18 |
| 91 | 28 |
| 115 | 100 |

-continued

| m/e | Relative Intensity (%) |
|---|---|
| 116 | 93 |
| 117 | 56 |
| 144 | 44 |
| m 192 | 18 |

Figure 3:
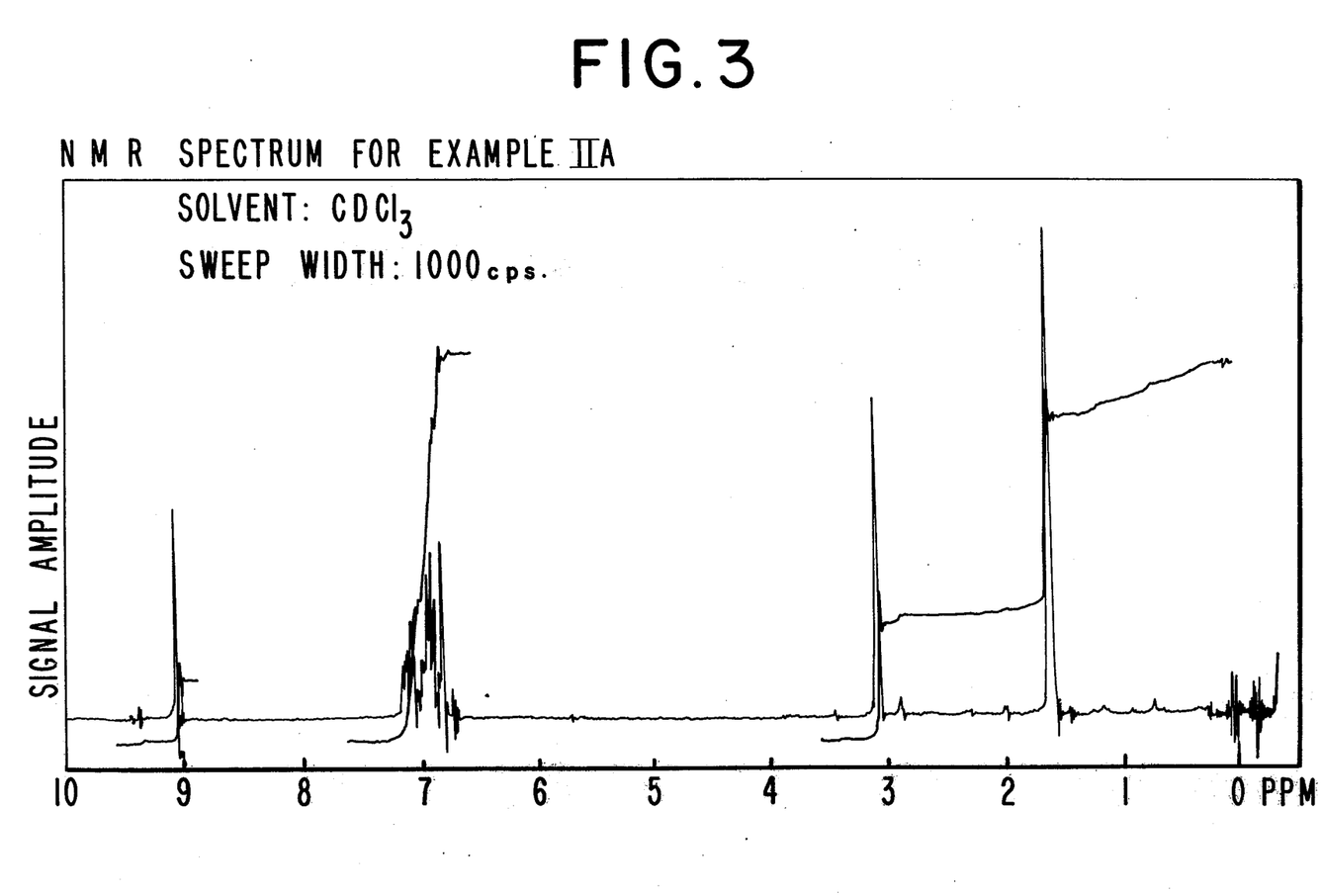
FIG. 3 illustrates the NMR spectrum of the cis isomer produced according to Example IIA.
Figure 4:
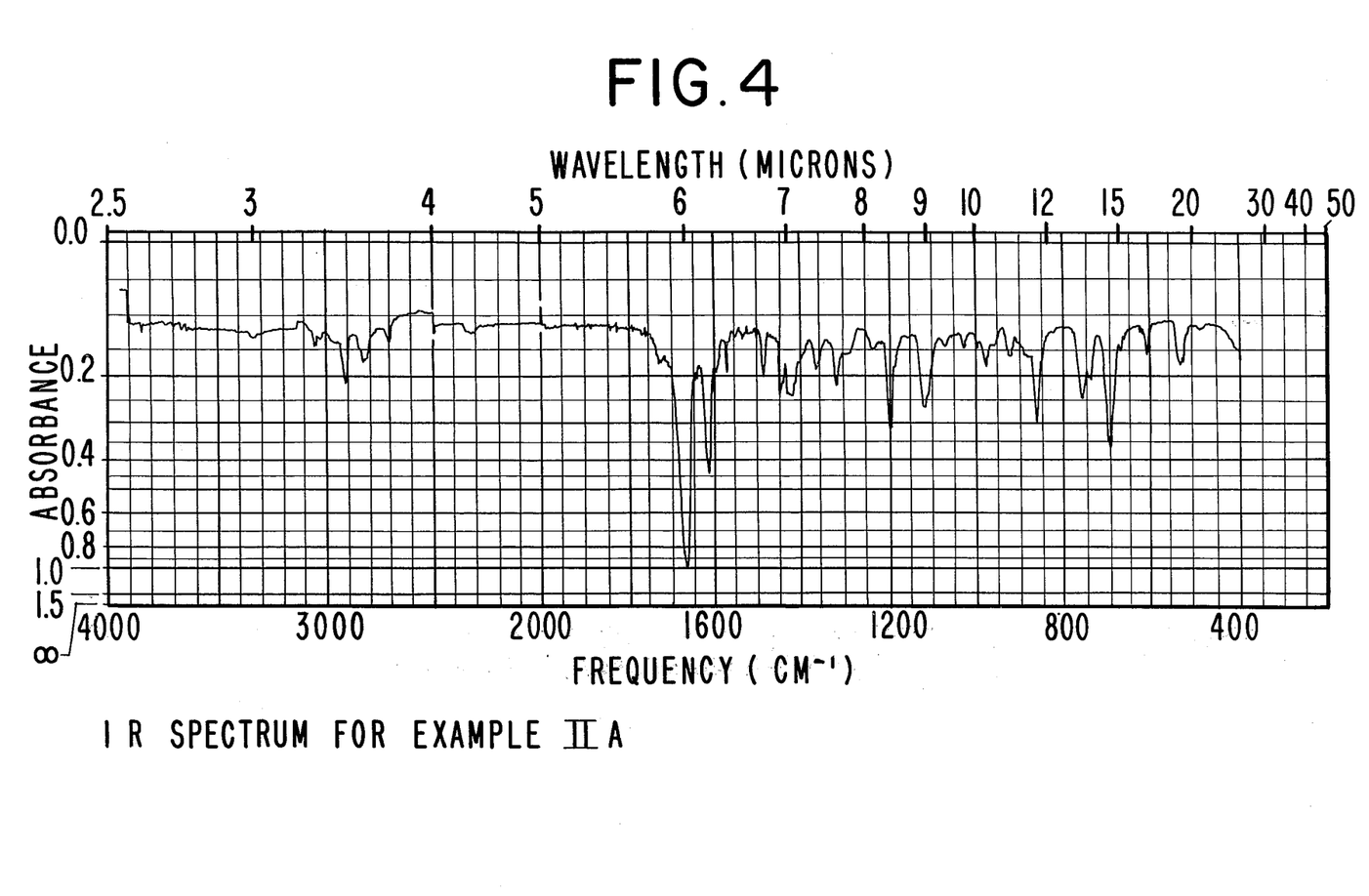
FIG. 4 illustrates the Infrared spectrum of the cis isomer produced according to Example IIA.

The NMR spectrum is set forth in FIG. 3. The Infrared spectrum is set forth in FIG. 4.

All of the above data confirms that 100% cis-2-[(methylthio)methyl]-3-phenyl-2-propenal is formed.

EXAMPLE IIB

PREPARATION OF A MIXTURE OF 87% CIS AND 13% TRANS 2-[(METHYLTHIO)METHYL]-3-PHENYL-2-PROPENAL

REACTION:

(87% cis isomer)  (13% trans isomer)

| EQUIPMENT: | CHEMICALS: |
|---|---|
| 2 liter Reaction flask | 4.77 gm Benzaldehyde - 4 1/2 moles. |
| 250 ml Addition funnel | |
| Mechanical stirrer | 416 gm Methional - 4 moles |
| "Y" adapter | 320 ml 25% NaOH - 2 moles |
| Thermometer | 900 ml 10% Sulfuric acid |
| Friedrichs Condenser | 700 ml Methylene chloride |
| 2" 29/42 Splash column | 900 ml sat. Sodium bicarbonate |
| Fraction Collector | 2000 ml sat. Sodium chloride |
| Rushover head | 1000 gm Sodium sulfate |
| 1 liter Distillation flask w/mantle | |
| 4 liter Separatory funnel | |
| Isopropanol/Dry Ice Cold Bath | |

PROCEDURE

1. Four moles of methional and 4½ moles of benzaldehyde are place in a 2 liter reaction flask fitted with a 250 ml addition funnel, Friedrichs condenser, Y-adapter, thermometer, and mechanical stirrer and cooled to 0° C. at which time dropwsie addition of 25% NaOH solution is begun.
2. The reaction mass temperature is maintained at 0° C. Total addition time is 1.25 hours.
3. The reaction is then permitted to warm to 20° C. and is stirred for an additional 3 hours.
4. The reaction mass is transferred to a 4 liter separatory funnel and 500 ml of methylene chloride are added. An emulsion is formed which is treated with 300 ml of 10% H$_2$SO$_4$, carefully separated, and a second 300 ml aliquot of 10% $H_2SO_4$ is added thereby permitting the emulsion to be extracted.
5. The aqueous acid layers are combined and extracted with 500 ml of methylene chloride.
6. The methylene chloride layers are combined and washed with 300 ml of 10% $H_2SO_4$, 3×300 ml of sat. $NaHCO_3$, and 1000 ml of NaCl brine.
7. The last wash is permitted to stand overnight at which time it is drained and extracted a second time with 1000 ml of NaCl brine.
8. The product is dried over sodium sulfate and the methylene chloride is stripped on a rotary evaporator.
9. The reside is subjected to rush-over distillation using a 2" splash column and Fraction 4 (88%) is again subjected to rush-over distillation to obtain a yellow liquid in Fraction 2–5 boiling at 151° C. at 3.8 mm Hg. The cis:trans isomer mixture was determined to be 87:13 by NMR analysis (FIG. 6).

The distillation fractions are as follows:

| Reaction No. | Vapor Temp. | Liquid Temp. | Vac. mm. Hg | Wt. of fraction g |
|---|---|---|---|---|
| (First Rushover Distillation) | | | | |
| 1-1 | 51 | 119 | 3 | 203.3 |
| 1-2 | 127 | 172 | 4 | 59.7 |
| 1-3 | 159 | 183 | 5 | 38.4 |
| 1-4 | 150 | 222 | 5 | 216.1 |
| 1-5 | 163 | 250 | 5 | 36.7 |
| Fraction 1–99.9% Benzaldehyde (Second Rushover Distillation) | | | | |
| 2-1 | 56 | 121 | 1.5 | |
| 2-2 | 117 | 144 | 1.6 | 17.6 |
| 2-3 | 126 | 150 | 1.8 | 5.8 |
| 2-4 | 149 | 162 | 3.5 | 46.7 |
| 2-5 | 151 | 168 | 3.8 | 108.00 |
| 2-6 | 149 | 177 | 3.8 | 14.6 |

Figure 5:
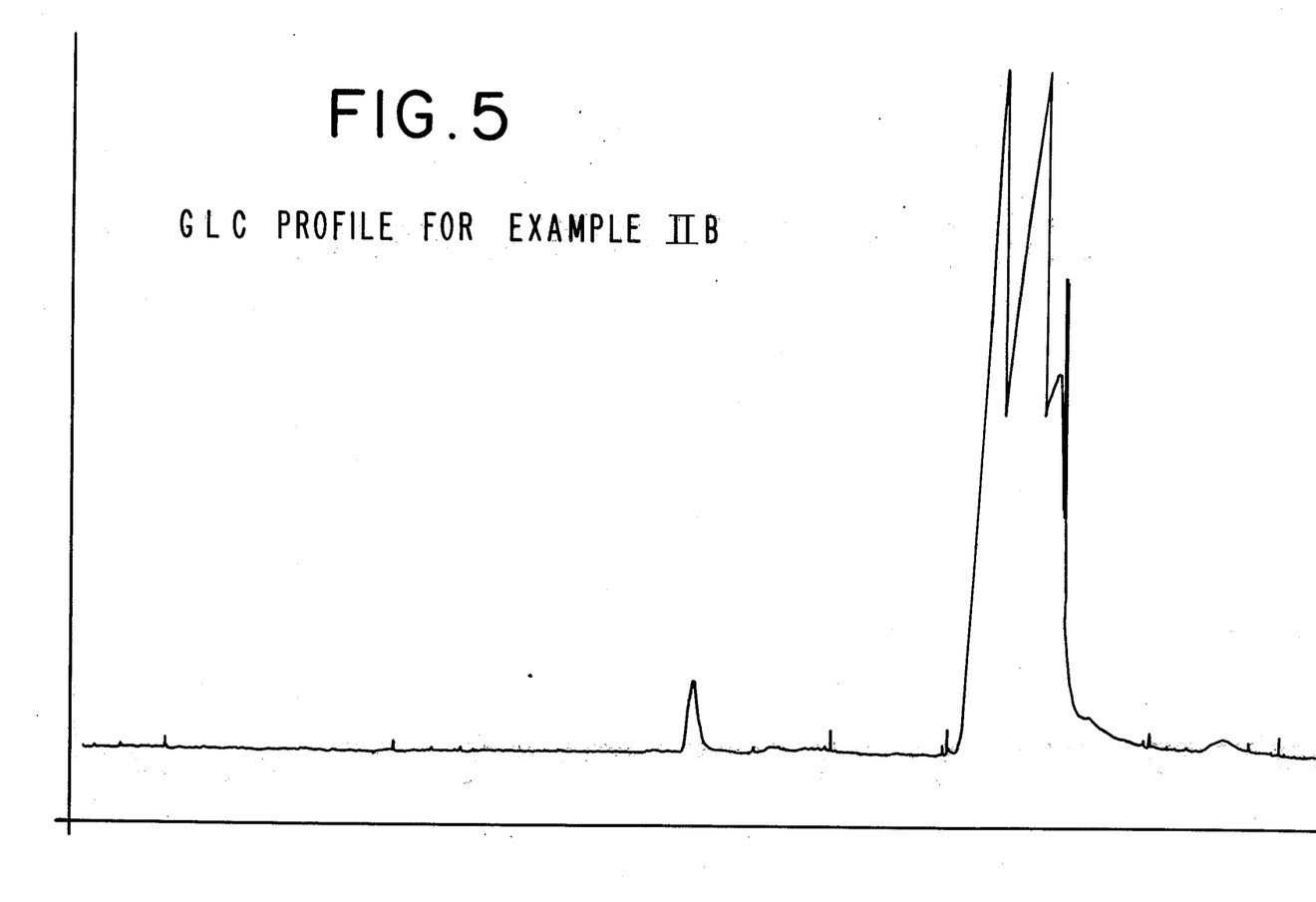
FIG. 5 illustrates the GLC profile of the 87:13 (cis:trans) mixture of isomers produced according to Example IIB.
Figure 6:
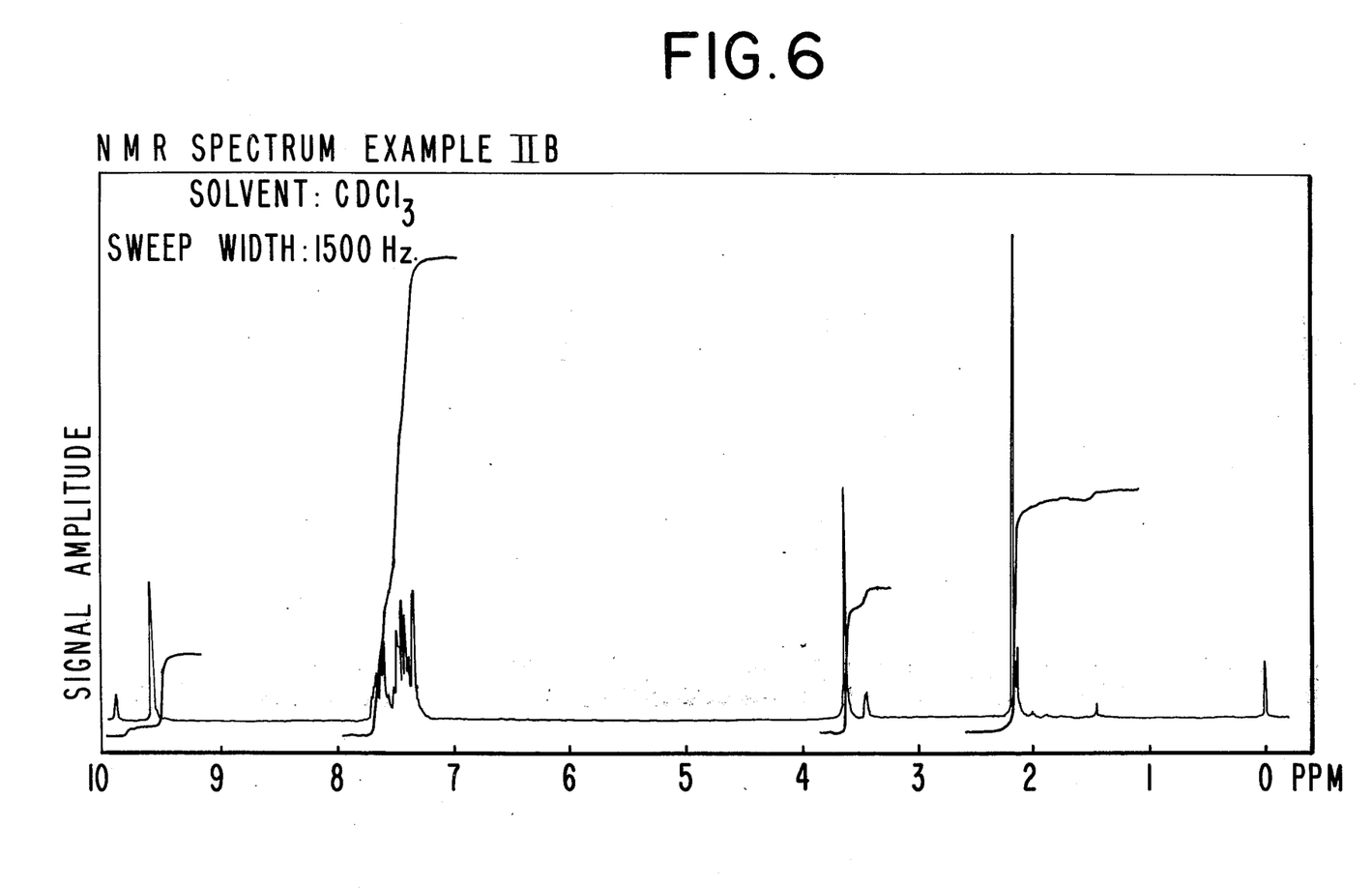
FIG. 6 represents the NMR spectrum for the 87:13 (cis:trans) mixture of isomers produced according to Example IIB.
Figure 7:
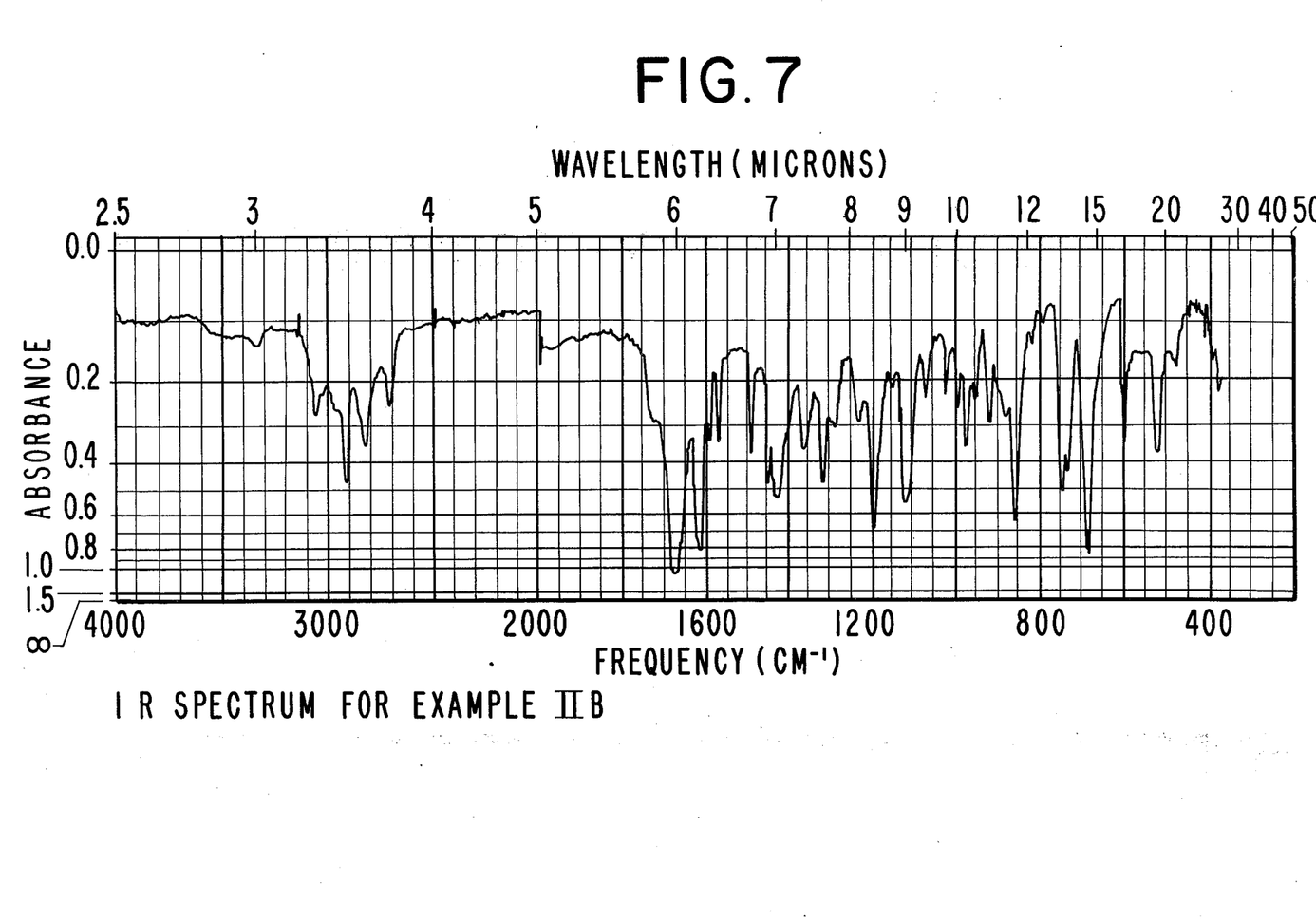
FIG. 7 represents the IR spectrum for the 87:13 (cis:trans) mixture of isomers produced according to Example IIB.
Figure 8:
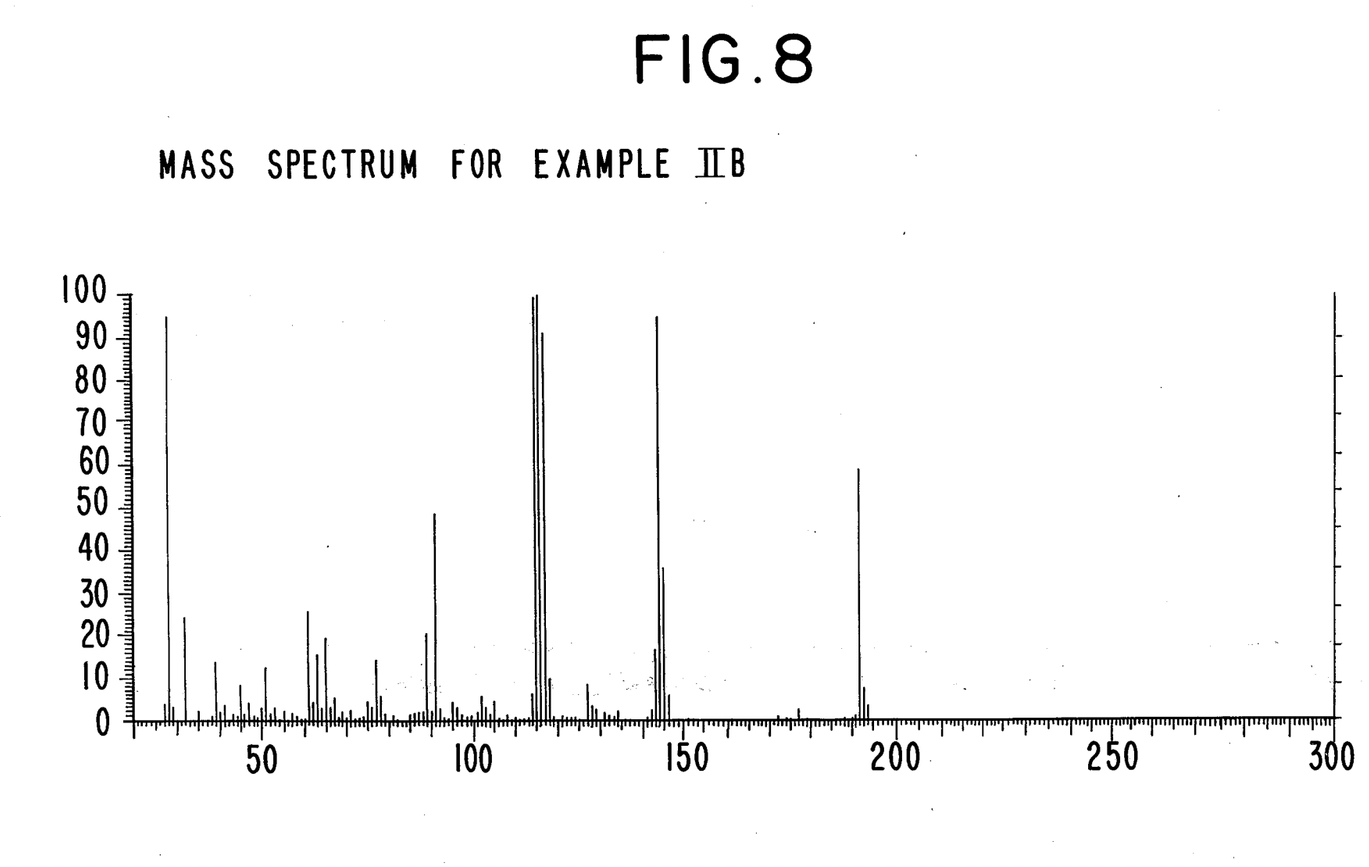
FIG. 8 represents the Mass Spectrum for the 87:13 (cis:trans) mixture of isomers produced according to Example IIB.

The GLC profile (conditions: 12 ft.×⅛ in. 5% SE 30 on 100–120 mesh Chromosorb G, programmed at 110°–190° C. at 4° C. per minute) is set forth in FIG. 5. the NMR spectrum is set forth in FIG. 6. The IR spectrum is set forth in FIG. 7. The Mass spectrum is set forth in FIG. 8.

EXAMPLE III

The 87:13 cis-trans isomer mixture of 2-[(methylthio)methyl]-3-phenyl-2-propenal prepared according to Example IIB is dissolved in propylene glycol to provide a 0.1% solution. This solution in the amount of 0.9 g is added to 7.3 g of a soup base consisting of:

| Ingredient | Parts by Weight |
|---|---|
| Fine ground sodium chloride | 35.5 |
| Hydrolyzed vegetable protein | 27.5 |
| Sucrose | 11.0 |
| Beef fat | 5.5 |
| Sethness caramel color (powder B & C) | 2.7 |

The resulting mixture has a hydrolyzed vegetable protein-like meaty, beef broth-like aroma and flavor with an excellent mouthfeel with an enhanced effect as when monosodium glutamate (18 gm) is added thereto even though the monosodium glutamate is absent from the mixture.

EXAMPLE IV 330 grams of gelatin is dissolved at 40° C. in 8,250 grams of deionized water to form a "gelatin solution."

600 cc of 5% acetic acid is then added. 330 grams of spray-dried gum arabic is dissolved at room temperature in 8,250 grams of deionized water to form a "gum arabic solution."

The gum arabic solution is placed in a 30 liter vessel and 2.5 liters of the gelatin solution is added. The temperature of the mixture is adjusted to 37° to 40° C. Through a tube beneath the surface of the gum arabic solution, 4,000 grams of 0.1 percent (by weight) solution of the 87:13 cis-trans isomer mixture of 2-[(methylthio)methyl]-3-phenyl-2-propenal prepared according to Example IIB in propylene glycol is added over a period of approximately 30 minutes.

The mixture is agitated at 37° to 40° C. until an average droplet size of 25 microns is obtained. The remaining gelatin solution (6 liters) is then added. The pH of the solution is then adjusted to 4.5 to 4.6 with a 10 percent sodium hydroxide solution.

After the 25 micron droplet size is achieved, the temperature is allowed to drop to 25° C. over a period of approximately 25 hours while maintaining the pH at 4.5 to 4.6.

The capsule slurry is then cooled to 5° C. with stirring and is maintained at 5° C. with stirring, for at least 2.5 hours. The slurry is then sprayed-dried.

The capsules thus formed are filtered and mixed with the soup base of Example III in the weight ratio of 1:6. 20 grams of the resulting capsule soup base mixture is then added to 30 ozs. of boiling water thereby creating a soup having an excellent meaty flavor.

The resulting mixture has an excellent meaty, beef broth-like aroma and flavor with an excellent mouthfeel and an enhanced effect as when monosodium glutamate is added thereto, even though the monosodium glutamate is absent from the mixture.

What is claimed is:
1. A mixture of substantially pure, synthetically produced cis and trans isomers of 2-[(methylthio)methyl]-3-phenyl-2-propenal having the structures and the ratio of cis to trans isomer being from 7:3 up to 9.5:0.5.

2. The mixture of claim 1 wherein the cis-trans isomer ratio is about 87:13.

3. A process for augmenting or enhancing the aroma or taste of a foodstuff comprising adding to said foodstuff from about 0.02 parts per million up to about 50 parts per million by weight based on the total quantity of foodstuff of the mixture of claim 1.

4. A process for augmenting or enhancing the aroma or taste of foodstuff comprising adding to said foodstuff from about 0.02 parts per million up to about 50 parts per million by weight based on total composition of the composition of claim 2.

5. A composition capable of augmenting or enhancing the taste or aroma of a foodstuff comprising:
(i) from about 0.1% up to about 15% per weight based on the total weight of said flavor and composition of the composition defined according to claim 1; and
(ii) the remainder of said composition being at least one adjuvant selected from the group consisting of:
Acetaldehyde;
Isobutyraldehyde;
Isovaleraldehyde;
Methyl sulfide;
Methyl disulfide;
Isobutyl acetate;
Phenylethyl acetate;
Diacetyl;
Acetophenone;
Furfural (50%);
Benzaldehyde;
Phenylacetaldehyde;
Isoamyl alcohol;
Phenylethyl alcohol;
Gamma-butyrolactone;
3-Phenyl-4-pentenal;
3-Phenyl-3-pentenal;
3-Phenyl-2-pentenal;
Methyl pyrazine;
Tetramethyl pyrazine;
Trimethyl pyrazine;
2,6-Dimethyl pyrazine;
2-Ethyl-3-methyl pyrazine;
2-Ethyl-3,5-dimethyl pyrazine;
2-Ethyl-3,6-dimethyl pyrazine;
2-Ethyl-5-methyl pyrazine;
2-Ethyl-3-acetyl pyrazine;
2-(i-butyl) thiazole;
2-(i-propyl) thiazole;
2-(n-propyl) thiazole;
2-Phenyl-4-pentenal;
2-Phenyl-4-pentenaldimethylacetal;
4-Methylthiobutanal;
trans-2-hexenal;
Hydrolyzed vegetable protein;
Monosodium glutamate;
Black pepper oil;
Nutmeg oil;
Celery oil;
Lemon oil; and
Mustard oil.

6. A composition capable of augmenting or enhancing the taste or aroma of a foodstuff comprising:
(i) from about 0.1% up to about 15% per weight based on the total weight of said flavor and composition of the composition defined according to claim 2; and
(ii) the remainder of said composition being at least one adjuvant selected from the group consisting of:
Acetaldehyde;
Isobutyraldehyde;
Isovaleraldehyde;
Methyl sulfide;
Methyl disulfide;
Isobutyl acetate;
Phenylethyl acetate;
Diacetyl;
Acetophenone;
Furfural (50%);
Benzaldehyde;
Phenylacetaldehyde;
Isoamyl alcohol;
Phenylethyl alcohol;
Gamma-butyrolactone;
3-Phenyl-4-pentenal;
3-Phenyl-3-pentenal;
3-Phenyl-2-pentenal;
Methyl pyrazine;
Tetramethyl pyrazine;
Trimethyl pyrazine;
2,6-Dimethyl pyrazine;
2-Ethyl-3-methyl pyrazine;
2-Ethyl-3,5-dimethyl pyrazine;
2-Ethyl-3,6-dimethyl pyrazine;
2-Ethyl-5-methyl pyrazine;
2-Ethyl-3-acetyl pyrazine;
2-(i-butyl) thiazole;
2-(i-propyl) thiazole;
2-(n-propyl) thiazole;
2-Phenyl-4-pentenal;
2-Phenyl-4-pentenaldimethylacetal;
4-Methylthiobutanal;
trans-2-hexenal;
Hydrolyzed vegetable protein;
Monosodium glutamate;
Black pepper oil;
Nutmeg oil;
Celery oil;
Lemon oil; and
Mustard oil

* * * * *